United States Patent [19]
Obremski et al.

[11] Patent Number: 6,110,749
[45] Date of Patent: Aug. 29, 2000

[54] SYSTEM FOR SIMULTANEOUSLY CONDUCTING MULTIPLE LIGAND BINDING ASSAYS

[75] Inventors: Robert J. Obremski; John W. Silzel, both of Yorba Linda, Calif.

[73] Assignee: Beckman Coulter, Inc., Fullerton, Calif.

[21] Appl. No.: 08/923,786

[22] Filed: Sep. 4, 1997

Related U.S. Application Data

[63] Continuation of application No. 08/609,410, Mar. 1, 1996, abandoned.
[51] Int. Cl.[7] .......................... G01N 21/01; G01N 21/64; G01N 33/552; G02B 6/00
[52] U.S. Cl. .......................... 436/527; 356/244; 356/246; 356/317; 356/318; 385/12; 385/13; 385/244; 422/57; 422/82.05; 422/82.08; 422/82.11; 435/4; 436/501; 436/518
[58] Field of Search ...................................... 356/317, 318, 356/244, 246; 385/12, 13, 144; 422/57, 82.05, 82.08, 82.11; 435/4; 436/501, 518, 527

[56] References Cited

U.S. PATENT DOCUMENTS

| | | | |
|---|---|---|---|
| 3,996,345 | 12/1976 | Ullman et al. | 424/12 |
| 5,081,012 | 1/1992 | Flanagan et al. | 435/7.9 |
| 5,340,715 | 8/1994 | Slovacek et al. | 435/6 |
| 5,439,647 | 8/1995 | Saini | 422/82.11 |
| 5,512,492 | 4/1996 | Herron et al. | 436/518 |

FOREIGN PATENT DOCUMENTS

| | | |
|---|---|---|
| 0533302A1 | 3/1993 | European Pat. Off. . |
| WO 84/01031 | 3/1984 | WIPO . |
| WO 88/01058 | 2/1988 | WIPO . |
| WO 89/01157 | 2/1989 | WIPO . |
| WO 93/06241 | 4/1993 | WIPO . |
| WO 93/08472 | 4/1993 | WIPO . |
| WO 95/08772 | 3/1995 | WIPO . |

OTHER PUBLICATIONS

Harrick, N.J., *Internal Reflection Spectroscopy*, Harrick Scientific Corporation, N.Y., 1987, pp. 89–145.

Ekins, R.P., et al.; "Multianalyte Immunoassay: The Immunological "Compact Disk" of the Future"; Journal of Clinical Immunoassay; vol. 13, No. 4, Winter 1990, pp. 169–181.

Ekins, Roger P., et al.; "Developing Multianalyte Assays"; TIBTECH, vol. 12, Mar. 1994, pp. 89–94.

Ekins, R.P., et al.; "Multianalyte Microspot Immunoassay—Microanalytical 'Compact Disk' of the Future"; Clinical Chemistry, vol. 37, No. 11, 1991; pp. 1955–1967.

Ellerby et al., "Encapsulation of Protein in Transparent Porous Silicate Glasses Prepared by the Sol–Gel Method," Science, vol. 255, 1113–1115, 1992.

Van Der Loos et al., "Double Epi–illumination Microscopy with Separate Visualization of Two Antigens: A Combination of Epi–polarization for Immunogold–Silver Staining and Epi–fluorescence for Alkaline Phosphate Staining," J. of Histochemistry and Cytochemistry, 42(3), pp. 289–295, 1994.

Nakamura et al "flurescence Immunoassays", in, Manual of Clinical laboratory Immunology, 4th Ed., Rose et al, eds., ASM, Washington, D.C., pp. 10–17, Jan. 1, 1992.

*Primary Examiner*—Rodney P. Swartz
*Attorney, Agent, or Firm*—William H. May; Margaret A. Kivinski

[57] ABSTRACT

A system for simultaneously conducting multiple ligand assays on a sample potentially containing target analytes uses as a detector a waveguide having a planar surface with a plurality of probes of known recognition to the target analytes thereon. The probes are in discrete areas on the waveguide. A sample containing target analyte is treated with a light-responsive compound such that it binds to the target analyte to form a conjugate and the conjugate is applied to the probes on the waveguide. A laser light is passed into the planar surface of the waveguide at a plurality of different locations, by causing relative movement between the waveguide and the laser light, so that evanescent waves radiate from the waveguide. Where conjugate has attached to a probe, there is emission of light different from that emitted by a probe without conjugate attached thereto.

23 Claims, 7 Drawing Sheets

SYSTEM FOR SIMULTANEOUSLY CONDUCTING MULTIPLE LIGAND BINDING ASSAYS

CROSS-REFERENCE

This application is a continuation of application Ser. No. 08/609,410 filed on Mar. 1, 1996 now abandoned.

BACKGROUND

This invention is directed to analysis of a biological fluid sample.

Health care costs consume a significant percentage of the gross national product. A substantial portion of the cost of health care is attributed to laboratory testing, which can be labor-intensive. Such laboratory testing can involve testing for multiple analytes in a patient's blood, urine, or spinal fluid.

Time is of the essence in laboratory testing. In certain instances, the successful treatment of a patient requires quick results from laboratory tests.

Sensitivity is also important in laboratory tests. Oftentimes, a substance of interest is present in minute quantities. In many situations, accurate diagnosis of a patient's condition requires the ability to detect these minute quantities. Existing testing systems are usually inadequate in that they suffer from at least one of the following disadvantages: high cost, slow results, or low sensitivity.

Accordingly, there is a need for a system for economically analyzing biological fluids which (1) is low cost; (2) provides quick results; and (3) can detect small quantities of analytes.

SUMMARY

The present invention is directed to a system that satisfies these needs. In particular, this system inexpensively and quickly detects analytes at low concentrations, and is so sensitive, can determine the entire mass of an analyte in a specimen. The system can simultaneously test for multiple analytes or can test multiple samples for a single analyte. The system has the added advantage that it can be automated with non-complex machinery.

The system includes a method for detecting a target analyte in a sample utilizing a unique detector, which comprises a waveguide having thereon a plurality of discrete probes. The waveguide generally is planar, i.e., is a sheet of plastic material. Each probe includes a specific binding partner for a selected analyte, and at least one of the probes is a responsive probe that includes a specific binding partner for the target analyte. Preferably the specific binding partner is covalently bonded to the waveguide. The sample is applied to the detector such that the target analyte binds to its specific binding partner. Preferably at least some of the water in the sample is removed from the detector. Laser light is then passed into the detector, preferably into one of the planar surfaces as a slit-shaped beam so that evanescent light radiates from the waveguide and impinges on the probes. Any light emitted from a probe with target analyte bound thereto is different from the light, if any, emitted by the same probe without target analyte bound thereto. Emission of light from the probes is detected, and from such detection, the presence or absence of the target analyte in the sample can be determined, as well as the concentration of the analyte in the sample.

This differential in light emission can be effected by attaching a light-emitting compound, such as a fluorophore, to the target analyte, either before or after it binds to its specific binding partner. The light-emitting compound emits light when the laser light is passed into the detector. For example, the fluorophore can be bound to a second specific binding partner for the target analyte, wherein a sandwich is formed on the detector in the sandwich comprising the fluorophore, the second specific binding partner, the target analyte, and the specific binding partner.

Alternatively, the probes can include a light-emitting compound, where the presence of the target analyte binding to the probe affects the light emitted by the light-emitting compound.

In another version of the invention, instead of using a light-emitting compound, a light-modulating compound, such as a fluorophore quencher or an enhancer, can be attached to the target analyte, where the probe has pre-attached to it a light-emitting compound whose light-emitting properties are affected by the light-modulating compound.

The system of the present invention can be used for screening multiple samples for the selected target analyte. This can be effected by using different light-emitting compounds for attachment to the target analyte in different samples, wherein the different light-emitting compounds emit light having a detectable difference when exposed to the evanescent light.

This system also can be used for detecting multiple target analytes in a single sample. This is effected by using a detector having a plurality of different discrete probes, wherein at least some of the probes are capable of binding to target analytes in the sample. The sample is applied to the detector so that the target analytes bind to a corresponding specific binding partner. Laser light is passed into the detector so that evanescent light radiates from the waveguide and impinges on the probe, wherein light, if any, emitted from a probe with target analyte bound thereto is different from the light, if any, emitted by the same probe without target analyte bound thereto. By detecting the emission of light from the probes, it is possible to determine which of the target analytes are present in the sample.

Preferably, before passing the laser into the waveguide, a substantial portion of the sample is removed from the waveguide to increase accuracy of measurement. This can be effected by allowing the sample to drip off of the waveguide, only leaving a very thin film of sample. Alternatively, the waveguide can be substantially and completely dried by application of heat and/or moving air.

The laser light is introduced into a planar surface of the waveguide. The laser light is introduced at a plurality of selected locations, i.e., at least two different locations, by causing relative movement between the waveguide and the laser light. This preferably is effected by moving the waveguide while maintaining the laser light fixed. The waveguide can be moved in two dimensions, i.e., both along its length and its width for maximum sensitivity of measurement.

The present invention can be used both for qualitative analysis and quantitative analysis. For quantitative analysis, a known quantity of an analog of the target analyte can be applied to the detector for a competitive assay.

A preferred detector comprises a waveguide having first and second opposing surfaces. The index of refraction of the waveguide is greater than its surrounding medium. Accordingly, when a laser light is passed into the waveguide at an angle of incidence greater than a critical angle, evanescent waves radiate from the first and second surfaces. There are a plurality of probes of known recognition to selected target analytes in discrete areas on at least one of the surfaces of the waveguide. The waveguide preferably is substantially planar with the probes in a two-dimensional array, with a fluorophore included with the probes. For example, the probes can be a plurality of discrete spots printed onto the surface of the waveguide.

The present invention also includes an apparatus effective for transmitting the light from a laser light source, which typically emits an approximately pencil-shaped beam, to produce a beam that is slit-shaped and thus suitable for introduction across the entire width of the waveguide.

This system has the advantage of involving only a small number of simple steps which in turn facilitates automation by non-complex machinery. For example, in a preferred version of the invention, there are only four manipulative steps; i.e., (1) applying sample to a waveguide wherein a light-responsive compound has been included with the probes on the waveguide, (2) removing at least a portion of the sample from the waveguide, (3) passing a laser light into the waveguide, and (4) detecting emitted light.

The assay is sensitive enough to detect a target analyte at low concentrations, and even determine the total amount of target analyte in a sample. It has been demonstrated down to $10^{-13}$ molar. This invention provides a considerable time and cost advantage over prior art methods. As such, the invention is economical, time efficient and sensitive.

DRAWINGS

These and other features, aspects and advantages of the present invention will become better understood from the following written description of the invention, the appended claims and accompanying drawings where:

DESCRIPTION

The present invention is directed to a system for simultaneously conducting multiple ligand binding assays on a sample possibly containing target analytes, wherein a complex between a specific binding partner at a probe and target analyte is detected using evanescent waves and light-responsive compound or compounds.

Figure 1:
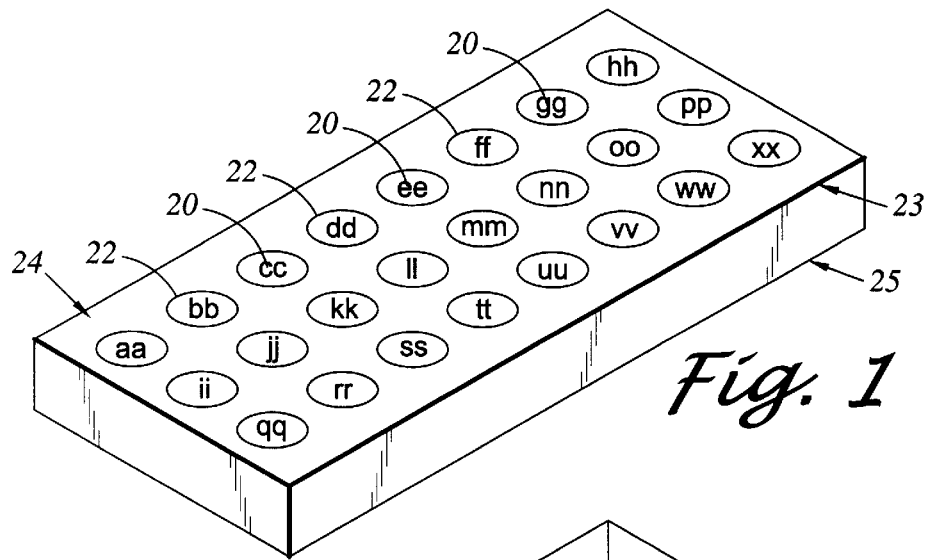
FIG. 1 is a perspective view of a waveguide according to the present invention with a two-dimensional array of probes in the shape of dots on a surface of the waveguide.

Referring to FIG. 1, a plurality of different probes 20 (designated by letters aa to xx) having specific binding partners are applied in discrete areas 22 onto the top 23 and bottom surfaces 25 of a planar waveguide 24. The waveguide 24 has an index of refraction greater than its surrounding medium, which is usually air. Each probe 20 includes a specific binding partner of known recognition to a selected target analyte; e.g., a monoclonal antibody, DNA oligonucleotide or enzyme cofactor. More than one probe can be bound to a particular analyte, i.e., there can be multiple probes responsive to an analyte such as Digoxin for improved sensitivity. In fact, all of the probes 20 can be responsive to a single analyte.

Figure 4A:
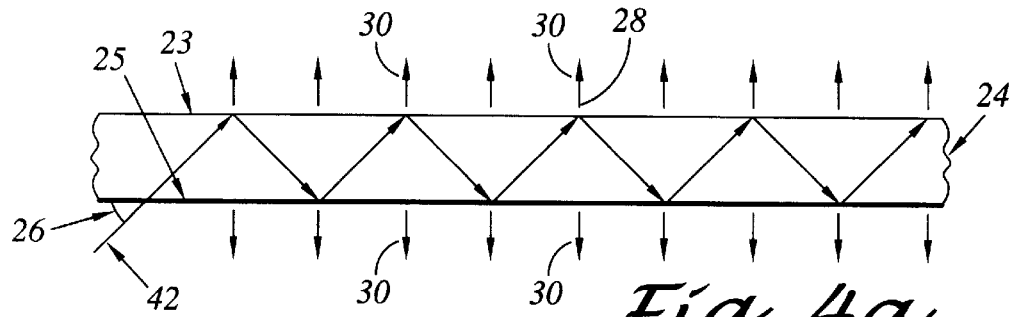
FIGS. 4A and 4B are cross-sectional views of the waveguides of FIGS. 1 and 2, respectively, showing light entering the waveguide at an angle greater than a critical angle.

A sample is applied to the waveguide 24 such that target analytes in the sample bind to the specific binding partner at a responsive probe. Referring to FIG. 4A, laser light 42 is passed into the waveguide 24 at an angle greater than a critical angle (defined below) so that there is total internal reflection 28 of the laser light and evanescent waves 30 radiate from the surface of the waveguide.

There are multiple variations of this system. In a first variation a light-emitting compound that is luminescent is pre-bonded to target analyte molecules (e.g., DNA/RNA, proteins, polysaccharides and the like) in the sample prior to applying the sample to the waveguide. At those discrete areas where a target analyte forms a complex with a responsive probe, light is emitted. This first version can be schematically represented as:

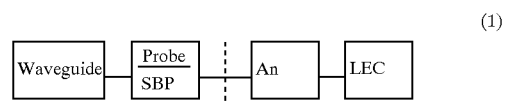

(1)

Wherein "SBP" stands for "specific binding partner; "An" stands for "target analyte" and "LEC" stands for "light emitting compound."

Multiple (at least two) light-emitting compounds which emit light at different wavelengths and which bond to different target analytes can be used. This allows simultaneous detection of different target analytes or samples with a single waveguide in a single test.

Alternatively, multiple light-emitting compounds which emit light at different wavelengths but bond to the same target analyte are used to simultaneously analyze multiple samples for the target analyte. For example, if the target analyte is present in the first sample, a first LEC emits, and if it is present in the second sample, a second LEC emits light at a different wavelength.

In a second variation, the light-emitting compound is included with the specific binding partner at each probe at each of the discrete areas, rather than being initially bonded to the target analyte. At those discrete areas where target analyte in sample has bonded to a specific binding partner at a probe, the emission of light is either enhanced or quenched.

This second version can be schematically represented as:

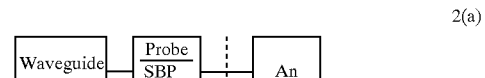

2(a)

2(b)

where "LMC" stands for "light modulating compound"; i.e., a light enhancer, quencher or wavelength shifter. In this second variation, the waveguide is provided with a probe that includes the LEC and a specific binding partner for the target analyte. In the detection step, the analyte alone (2(*a*)) or the analyte with a LMC (2(*b*)) is attached to the SBP.

Multiple different light modulating compounds having different modulating effects can be used to simultaneously detect multiple target analytes in the sample. LMCs that cooperate with one another are selected; i.e., the effect of one does hinder or cancel out the effect of another. This can improve the detection and discrimination between different target analytes as well as to further facilitate the simultaneous assay of different classes of target analytes. The different LMCs bond to different target analytes or samples and modulate the LEC differently.

Alternatively, different LMCs with different modulating effects can be used for bonding to the same target analyte but in different samples. This variation provides for the simultaneous assay of different samples for the target analyte.

In a third variation of the invention, after applying the sample to the waveguide, a developer is applied to the waveguide. The developer comprises a light-emitting compound, which attaches to the target analyte bonded to a specific binding partner to form a conjugate or sandwich.

The system can be used for quantitative competitive assay. For example, the developer can include a known quantity of an analog of the target that competes with target analyte to bond to the probe. Thus, the target analyte and the analog bind to the probe in a proportion based on their respective concentrations. The waveguide is treated with a light-emitting compound which is specific for attaching to the target analyte but does not bond to the analog. The greater the amount of target analyte which bonds to the probe, the more light-emitting compound is present at the probe and the stronger the light emission signal.

Alternatively, the light-emitting compound can be specific for attaching to the analog rather than the target analyte. Consequently, the greater the concentration of target analyte compared to the analog concentration, the lower the signal strength. A calibration curve is used to convert signal strength to concentration of target analyte.

This third variation can be schematically represented as:

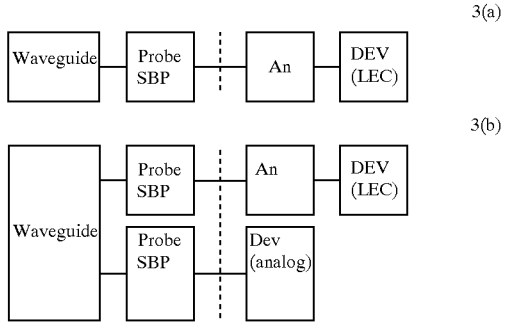

wherein "Dev" stands for "Developer". Schematic 3(*a*) depicts a qualitative binding assay, and schematic 3(*b*) depicts a quantitative competition assay.

Waveguide—The waveguide 24 is a substantially optically transparent, planar sheet of material. It has a sufficiently high refractive index relative to its surrounding medium that it contains incident light that impinges upon it and transmits the light when the angle of incident light is greater than the critical angle. The critical angle 26 is the arcsine of the quotient of the refractive index of the surrounding medium divided by the refractive index of the waveguide 24. Under these conditions an electromagnetic field radiates beyond the surface of the waveguide. This field, which is known as an evanescent wave, penetrates into the surrounding medium and has the ability to excite a light-emitting compound (e.g., a fluorophore) on the surface of the film. The "evanescent wave" is that portion of the light which can interact with matter beyond the surface of the waveguide.

Referring to FIG. 4A, the waveguide 24 is made out of a light-conducting material which is sufficiently free from light-absorbing materials at the laser wavelength to avoid undue interference with the laser light passing through it. In a preferred embodiment of this invention, the waveguide 24 is planar. The refractive index of the waveguide material is greater than its surrounding medium, air, so that a laser beam 42 passed into the waveguide at an angle greater than the critical angle 26 is contained within the waveguide 24 and the evanescent waves 30 are present at the surfaces of the waveguide.

In qualitative terms, the larger the refractive index of the waveguide, (1) the better its ability to contain the laser beam; (2) the smaller the penetration of evanescent wave into the surrounding medium; and (3) the larger the launch angle to contain the beam within the waveguide. These factors are competitive. For example, a larger index of refraction is desirable to contain the beam; however, a smaller index of refraction is desirable for greater penetration by the evanescent waves. The material selected as a waveguide is based upon a tradeoff off of these competing factors.

The waveguide need not be made of optical quality material, and can in fact be made of relatively inexpensive plastic sheet. Typical materials for the waveguide are polystyrene, polypropylene, borosilicate (glass) and polycarbonate. Polystyrene is a preferred material due to its compatibility with long wavelength light in the near infrared range of the spectrum and its established efficacy and common use as an immunochemical substrate. Polystyrene waveguide material is commercially available from Polyfiltronics, Inc. 100 Weymouth Street, Rockland, Md. 02370.

Referring to FIG. 4A, thinner waveguides are more desirable than thicker waveguides. This is because thinner waveguides result in more bouncing of the laser beam off the first and second surfaces of the waveguide. This is known as a "higher mode of propagation" in the waveguide. A higher mode of propagation results in a better generation of evanescent waves 30 radiating from the full surface of the waveguide with a minimization to elimination of dark spots. The waveguide can be as thick as about 100 mils. Ideally, the waveguide is between about 1 mil to about 10 mils thick.

Referring to FIG. 1, typically the waveguide 24 is either rectangular or square shaped in cross-section. For a rectangular waveguide that can be used as a dipstick, the length of waveguide can be about 1 inch to about 4 inches with a preferred length of 3 inches. The width of the waveguide is from between about 0.1 inches to about 1 inch with a preferred width of 0.25 inches.

Longer waveguides can be used; however, as the length of the waveguide increases, there is a dropoff in laser beam intensity and a problem with the waveguide sagging. Some sag in the waveguide adversely affects the sensitivity or effectiveness of the assay.

As discussed below, the dropoff problem can be overcome by causing relative movement between the waveguide and the laser light, such as by moving the laser beam along the length of the waveguide, or moving the waveguide relative to a fixed laser beam.

As technology for applying probes (described below) in discrete areas improves, the size of the waveguide can be reduced to that of a typical U.S. postage stamp and even smaller.

Optionally, channels or wells can be included in the waveguide to cordon the waveguide off into areas. The channels can be formed by selectively coating the waveguide to control surface tension so that the sample pools in the selected channels or wells. This can be effected by either (i) a chemical or vapor deposition of a light-blocking material; (ii) printing on the waveguide; or (iii) use of a hydrophobic agent. The advantage of channels is to confine liquid samples to desired areas of the waveguide, or confine light to desired areas. This is useful in the simultaneous assay of multiple samples, as well as multiple target analytes.

Probes—Referring to FIG. 1, the probes 20 include a specific binding partner, and can consist essentially of a specific binding partner bound to the waveguide. A specific binding partner is a first molecule which forms a complex or conjugate with a second molecule or substance referred to as the target analyte. The specific binding partner has a site which has a high avidity and affinity for the target analyte. High avidity means that the site specifically binds the target analyte to the exclusion of other substances, and high affinity Suitable molecules which are excited by evanescent waves to emit light are fluorophores; namely, phthallocyanine dyes, LaJolla Blue (Si phthallocyanine with PEG axial ligands), fluorescein isothiocyanate ("FITC"), rhodamine isothiocyanate; 2, 4-dinitrofluorobenzene, phenylisothiocyanate, dansyl chloride, substituted rhodamine isothiocyanates ("XRITC"), tetraethyl rhodamine isothiocyanate ("TRITC"), cadaverine ("TRAP") and phycobiliproteins (e.g., allophycocyanin, HDITCP (1,1', 3.3.3', 3' hexamethyl-4,4', 5.5' dibenzo-2,2' indotricar bocyanine percholoate), and phycoerythrin) fluorophores discussed in U.S. Pat. No. 4,877,965, which is incorporated herein by reference, and the molecule illustrated herein below which has a carboxy acid tail for conjugation and is commonly known as DBCY5.

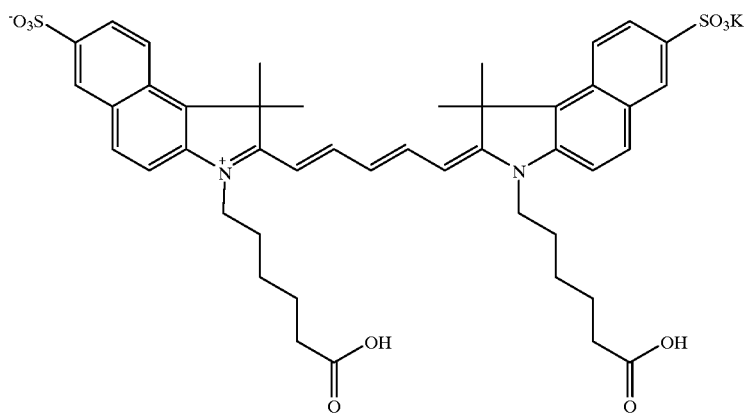

means a strong association to the target analyte. The specific binding partner ("SBP") can be naturally occurring or artificially formed.

Many of the compounds conventionally used in diagnostic procedures as specific binding partners can be used for the probes 20. Exemplary specific binding partners include:

(1) Single stranded polynucleotides of DNA ("deoxyribonucleic acids") and RNA ("ribonucleic acids")—The SBP's have a length between about 5 bases to about 25 bases with a preferred length of about 12 bases. These sbp's hybridize to a single stranded DNA or RNA in the sample;

(2) Antibodies and fragments of antibodies—The antibodies are of any of the various classes or subclasses of immunoglobulin, e.g., IgG, IgA, IgM, IgD and IgE, and of either human or animal origin, such as sheep, rabbits, goats and mice. In addition to intact antibodies, antigen binding fragments are usable; e.g., Fab Fab' and Fab'$_2$. The antibodies or fragment can be produced by hybridoma technology, cloning and expression or display on a bacteriophage;

(3) Enzymes, receptors and other proteins having a binding site specific to a selected molecule.

Light-responsive, light emitting and light-modulating compounds—The term "light-responsive compound" refers to two types of molecules. First, it refers to molecules which are excited by evanescent waves so as to emit light; i.e., light emitting compounds. Second, it refers to molecules which do not necessarily emit light themselves; rather, they enhance, quench or shift the wavelength of the excitation and light emission of another molecule. These light-responsive compounds are called "light-modulating compounds". The effect of a light-modulating compound is to emit, quench, enhance or shift the wavelength of light.

Suitable molecules which are excited by evanescent waves to emit light that have a large avidity and are specific to double stranded nucleic acids are ethidium bromide, acridine orange (C.I. No. 46005), quinacrine, diethidium bromide, diacridine orange and various heterodimers of the foregoing. U.S. Pat. No. 5,268,486 to Waggoner discloses an arylsulfonate cyanine dye which bonds to DNA/RNA, and is incorporated herein by reference.

Suitable light-modulating compounds are cyclodextrins, $H_2O_2$, and other peroxide derivatives.

The following table presents light-modulating compounds useful in conjunction with various light-emitting compounds and the effect (associated property charge) of the light modulating compound.

| Light-Emitting Compound | Light-Modulating Compound | Effect | | |
|---|---|---|---|---|
| | | E | Q | WLS |
| fluorescein | cyclodextrin | ✓ | | |
| fluorescein | rhodamine | | | ✓ |
| DBCY5 | peroxide | | ✓ | |

Wherein "E" stands for "Enhance," "Q" stands for "Quench," and "WLS stands for "Wavelength Shift.

Figure 2:
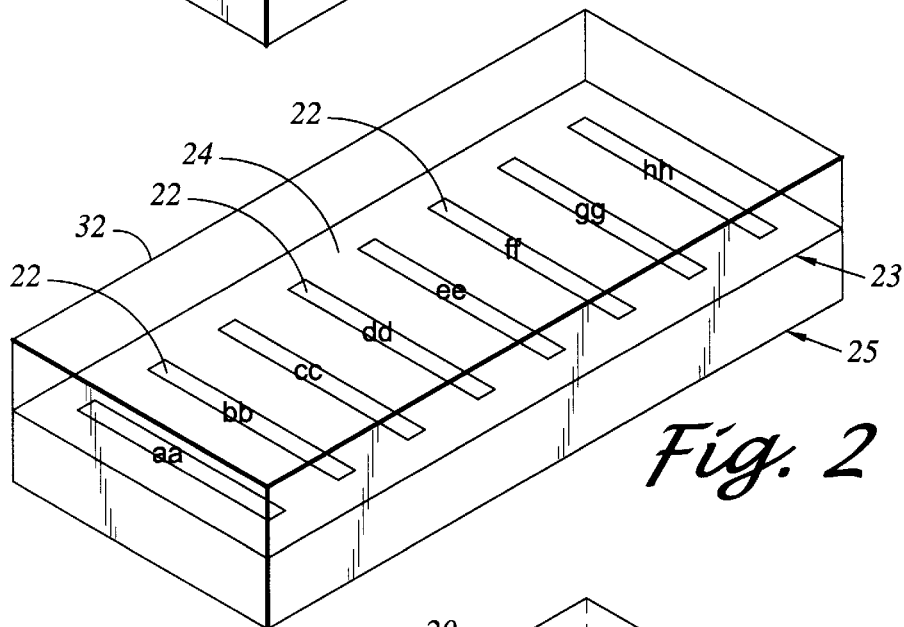
FIG. 2 is a perspective view of a second waveguide according to the present invention with spaced apart probe strips on the waveguide, with a sol gel overlayer.

Attaching probes to the waveguide—Referring to FIG. 2, the configuration of the discrete areas 22 on the waveguide surface can be an array of parallel strips. Referring to FIG. 1, a preferred configuration of discrete areas on the waveguide surface is a matrix of rows and columns of spots. The shape of the discrete areas 22 can be any shape which allows for detection by a detector; e.g., squares, triangles or stars. A preferred shape is spots (approximately circular) and strips (approximately rectangular). Spots are a more preferred shape to facilitate maximum use of the surface area of the waveguide.

Figure 3:
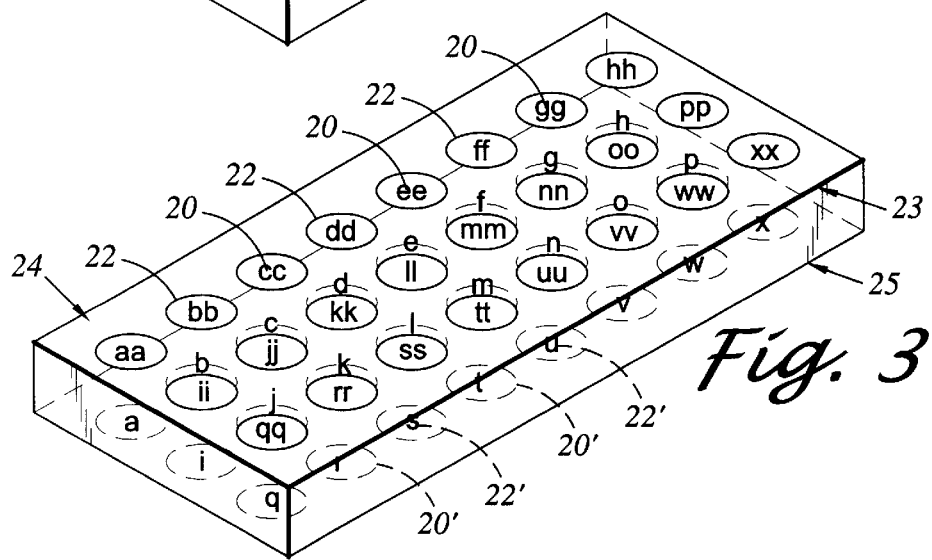
FIG. 3 is a perspective view of a third waveguide according to the present invention with dot-shaped probes on both surfaces of the waveguide.

The discrete areas 22 can be as small in size as the limit of the detection of the analysis. Typically, the limits of detection require a discrete area size of at least about $20\mu^2$ with 1:1 imaging optics. The probes are applied in discrete areas on at least one surface of the waveguide. Referring to FIG. 3, probes 20 and 20' can be applied to both surfaces of the waveguide.

U.S. Pat. No. 5,429,807 to Mattson et al., which has been assigned to the assignee of the present patent, Beckman Instruments, Inc. (Fullerton, Calif.), and is herein incorporated by reference, discloses a method suitable for applying probes in discrete areas on the waveguide. In particular, this patent discloses an automated method for performing macromolecule synthesis on a waveguide surface whereby a two-dimensional array of biopolymers in discrete areas are obtained on the surface.

Another method to apply probes in discrete areas on the waveguide is to use an ink jet printer. Typically, a commercial ink jet printer has about four jets which can each be loaded with a different probe. An ink jet printer intended for microfabrication of custom units typically has six jets which can be loaded with different probes. These commercial or microfabrication dedicated ink jet printers can be modified to provide for more "jets" so that a greater number of different probes can be applied in a single pass of the waveguide through the printer. The waveguide can be run through multiple ink jet printers wherein each ink jet printer applies probes. In the alternative, a stack of waveguide sheets are run through a single ink jet printer to apply probes. The jets are then cleaned and loaded with different probes and the process is repeated as many times as necessary.

For example, a band pass filter can be used on the light from the laser to be certain that only light of a desired wavelength passes into the waveguide, i.e., only light of a wavelength to which the dye is responsive. Similarly, an emission band filter can be provided between the waveguide and the detection apparatus, for filtering out the light of all wavelengths other than those expected to be emitted by the chosen fluorophore.

The following U.S. patents, which are incorporated herein by reference, disclose methods and apparatus for bonding polynucleotides and/or polypeptides to polypropylene, polystyrene, glass and other waveguide materials: U.S. Pat. Nos. 5,135,785 to Farnsworth; 4,065,412 to Dreyer; 4,704,256 to Hood; 4,603,114 to Hood; 3,652,761 to Weetal; 4,695,537 to Dorsett; 5,242,797 to Hirschfeld and 4,631,211 to Houghten. Methods for derivatization of polypropylene for bonding to polynucleotides are described in co-pending U.S. patent application Ser. No. 07/091,100, which has been assigned to the assignee of the present patent, Beckman Instruments, Inc. (Fullerton, Calif.), and is herein incorporated by reference.

Control probes can be used to test for error in running an assay. A control probe is responsive to control target analytes. One or more control probes are applied to the waveguide at discrete areas as previously described. The sample to be analyzed is spiked with control analytes. If the assay is functioning properly, there is a positive reading for the control analyte. Any failure to obtain a positive reading indicates a problem with the assay. The molecule used as a control is not a target analyte which is the subject of the analysis.

Figure 4B:
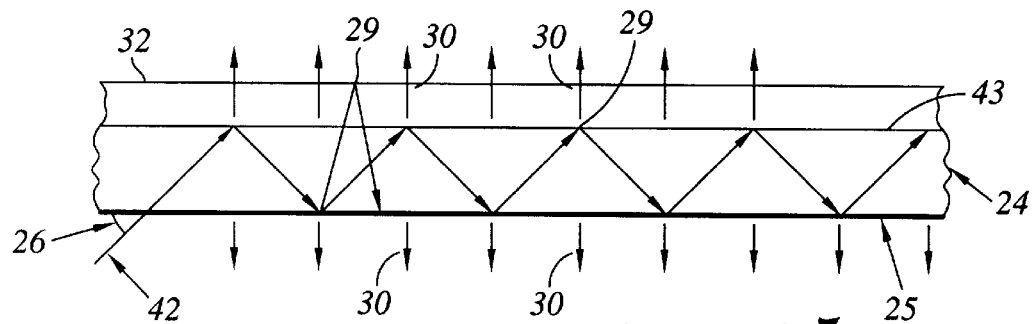

Water permeable overlayer—Referring to FIG. 2, optionally, a water permeable overlayer 32 can be applied to the surfaces 23 and 25 of the waveguide 24. Typically, the water permeable overlayer is a sol gel. Referring to FIG. 4B, the function of the water permeable overlayer 32 is to enhance the containment of the laser beam within the waveguide. In particular, there may be imperfections on the surfaces 23 and 25 of the waveguide (e.g., scratches and cuts) through which light can refract out of the waveguide. The water permeable overlayer 32 catches this escaping light and reflects it within the waveguide-water permeable overlayer complex.

Typical sol gels are transparent oxide glasses which transmit light and are permeable to water. Sol gels can be prepared by hydrolysis and polycondensation of alkoxides such as tetramethylorthosilicate. A typical method of preparation is discussed in *Science*, 255, 1113–1115 (1992) by Zink et al.

The refractive index of the sol gel can be modified by aging or mixing the composition with $TiO_2$ based materials.

The sol gel can be spin coated onto the waveguide. The spin coating can take place before or after contacting the waveguide with sample. Where the sol gel is spin coated on first, then the sample is applied on top of the sol gel and it permeates through the sol gel to the probes.

Figure 5:
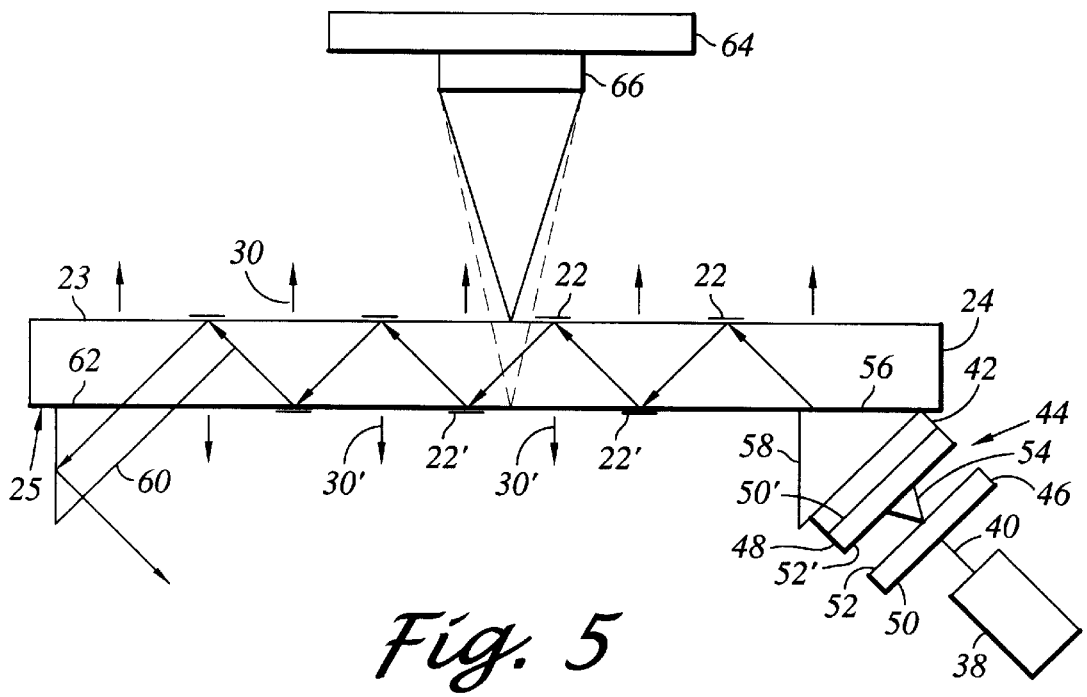
FIG. 5 is a schematic diagram of an apparatus for conducting analysis according to the present invention.

Multiple layers of probe on waveguide—Referring to FIG. 3, an embodiment of the invention is to apply a first set of probes 22 to the first surface 23 and second set of probes 22' to the second surface 25 of the waveguide 24. Referring to FIG. 5, when a laser beam 42 is passed into the waveguide 24, evanescent waves 30 and 30' radiate out of both the first surface 23 and second surface 25 of the waveguide and excite probe-sample complexes on both the first surface 23 and second surface 25 of the waveguide 24.

In another embodiment, probes are embedded in a three-dimensional array in a cube. The cube is a "layer cake" of waveguide with sol gel interspersed. In this case, the refractive index of the sol gel is made higher than that of the plastic so the sol gel becomes the waveguide.

Bonding light-responsive compound to sample or probe—Methods for bonding a light-responsive compound to target analytes in a sample and/or to a specific binding partner at a probe are well known to those of ordinary skill in the art, and include methods such as those described in L. M. Smith et al., *Nucleic Acids Research*, Vol. 213, p. 2399 (1985); B. S. Packard et al., *Biochemistry Biophysics ACTA*, Vol. 769, p. 2010208 (1984); P. K. Bhattacharyya et al., *Biochemistry Biophysics Research Communities*, Vol. 101, p. 273–280 (1981); H. Haigler et al., *Proceedings Of The National Academy Of Science U.S.A.*, Vol. 75, p. 3317–3321 (1978); M. J. Anderson et al., *Journal of Physiology*, Vol. 237, p. 385–400 (1974); R. D. Spencer et al., *Clinical Chemistry*, Vol. 19, p. 838–844 (1973); Y. Zagyansky et al., *Science*, Vol. 191, p. 466–468 (1976); A. N. DeBelder et al., *Carbohydrate Research*, Vol. 30, p. 375–378 (1973); T. Oonishi et al., *Journal of Immunological Methods*, Vol. 84, p. 143–154 (1985); Arriaga et al., *Anal. Chim. Acta*, 299:319–326, 1995; Chang et al., *Anal. Chem.* 67:959–966, 1995; Chang et al., *Anal. Chem.*, 67:959–966, 1995; Fadden et al., *Anal. Biochem.*, 225:81–88, 1995; Zakharov et al., *Anal. Biochem.* 224:195–198, 1995; Fukase et al., *J. Carbohydr. Chem.*, 13:715–736, 1994; Liu et al., *Bioorganic Chem.*, 22:29–35, 1994; Mansour et al., *Cytometry*, 15:272–276, 1994; Sikorski et al., *Tetrahedron Lett.*, 35:4275–4278, 1994; Starke et al., *Nucleic Acids Res.*, 22:3997–4001, 1994; V. V. Didenko, *Anal. Biochem.*, 213:75–78, 1993; Guldutuna et al., *Clin. Chim. Acta*, 214:195–207, 1993; Mansfield et al., *BioTechniques*, 15:274–279, 1993; Mujumdar et al., *Bioconjugate Chem.*, 4:105–111, 1993; Robertson et al., *J. Comp. Neurol.*, 328:485–500, 1993; Rothenberg et al., *Proc. Natl. Acad.S ci. USA*, 90:11939–11943, 1993; Wang et al., *Anal. Chem.*, 65:3518–3520, 1993; Williams et al., *Anal. Chem.*, 65:601–605, 1993; S. Hase, *J. Protein Chem.*, 11:387, 1992; Kobayashi et al., *Biosci. Biotechnol. Biochem.*, 56:186–189, 1992; Okano et al., *Anal. Biochem.*, 202:120–125, 1992;

Ragnarson et al., *Histochemistry,* 97:329–333, 1992; Y. Ran Kim et al., *Am. J. Clin. Pathol.,* 97:331–337, 1992; T. Sano et al., *Proc. Natl. Acad. Sci. USA,* 89:1534–1538, 1992; Schmitz et al., *Cytometry,* 13:478–484, 1992; J. Suzuki et al., *Clin. Chem.,* 38:752–755, 1992; Y. Tsuruta et al., *Chem. Pharm. Bull.* (Tokyo) 40:1626–1628, 1992; K. Yamaki et al., *Jpn. J. Pharmacol.,* 58:299–307, 1992; P. Zhuang et al., *Biotechnol. Prog.,* 8:204–210, 1992; J. Corsetti et al., *Anal. Biochem.,* 195:122–129, 1991; Diamandis et al., *Clin. Chem.,* 37:1486–1491, 1991; Friedman et al., *DiI. Brain Res.,* 560:297–302, 1991; Meadows et al., *J. Immunol. Methods,* 143:263–272, 1991; G. Patonay et al., *Anal. Chem.,* 63:321A–327A, 1991; A. Riggin et al., *Anal. Chem.,* 63:468–474, 1991; E. Sakal et al., *Biochem.,* 30:8899–8904, 1991; R. Shimazawa et al., *Biochem. Biophys. Res. Commun.,* 179:259–265, 1991; Y. Uchimura et al., *Gene,* 108:103–108, 1991; W. Volker et al., *J. Histochem. Cytochem.,* 39:1385–1394, 1991; J. G. Westmur, *CRC Crit. Rev. Biochem. Mol. Biol.,* 26:227–259, 1991; Yamada et al., *Anal. Biochem.,* 199:132–136, 1991; Oser et al., *Anal. Biochem.,* 191:295–302, 1990; and U.S. Pat. No. 5,268,486 to Waggoner which has already been incorporated by reference. A preferred technique to bond a fluorophore to a target analyte in the sample and/or probe is to put a long chain carboxylic acid tail on the fluorophore. The fluorophore can then be bonded to amino or spherical nucleophilic groups using a coupling agent such as carbodiimide.

The sensitivity and versatility of the assay can be increased by using multiple light-responsive compounds where (1) certain probes have one light-responsive compound associated with them and other probes have another light-responsive compound associated with them and/or (2) different light-responsive compounds are bonded to different samples. The term "light-responsive compounds" refers to both "light-emitting compounds" and "light-modulating compounds". Associating different light-responsive compounds with different probes facilitates a detector to discriminate between probes at different discrete areas. This is achieved, for example, through the different light-responsive compounds emitting light at different wavelengths. This improves the versatility and sensitivity of the assay in that a light-responsive compound best suited for interacting with a particular target analyte in a sample can be associated with the probe for that target analyte. Another light-responsive compound best suited for interacting with a second target analyte in the sample can be associated with the probe for the second target analyte.

Associating different light-responsive compounds with different samples allows for analyzing more than one sample at a time. This is achieved, for example, through the use of light-responsive compounds that emit light at wavelengths sufficiently different that a detector (discussed below) can discriminate between the wavelengths.

Laser light—Referring to FIG. 5, a laser light source 38 can be a near infrared ("NIR") laser, a visible light laser or ultraviolet ("UV") laser. Long wavelength light in the near infrared range is preferred in that long light reduces background noise and facilitates the use of charge coupled detectors ("CCD"). In wet samples (described below), the wavelength preferred is no longer than about 1000 nanometers in that longer wavelengths result in interference caused by the laser light interacting with water in the wet sample and the Si of a CCD being non-responsive when the sample is dried before detection. When the waveguide is dried before detection, because only the Si response is of concern, the preferred wavelength is from about 600 to about 960 nanometers. Short wavelengths in the ultraviolet range of the spectrum can also be used; but, ultraviolet light is not compatible to transmission through a polystyrene waveguide. The power output of the laser is from about 1 milliwatt to about 100 milliwatts. A diode laser (e.g., gallium arsenide) is a preferred laser light source. This is because diode lasers are commercially available, inexpensive and have suitable power.

Commercially available diode lasers that are suitable for use in this invention are gallium arsenide laser which emit laser light at 650, 660 or 670 nanometers sold by Toshiba (Tokyo, Japan) as Model Numbers TOLD9321, TOLD9412, TOLD 9520; 750, 790 and 810 nanometer lasers sold by Sharp Corp. (Osaka, Japan) as Models LTU16, LTU24, LTU31; and a laser with built-in optics sold by Lasiris, Inc. (St. Laurent, Quebec, Canada) as Model No. SNF 501-H.

The laser light source 38 emits a pencil-shaped beam 40 which needs to be reshaped into the slit-shaped light beam 42 that extends across the portion of the waveguide 24 having probes, which is preferably across substantially the entire width of the waveguide 24. An optical device 44 that is non-Gaussian is preferred for reasons of its simplicity. Such an optical device is disclosed in U.S. Pat. No. 4,826,299 and Canadian Patent, 1,276,829 which are incorporated herein by reference. The device utilizes prisms to achieve a "line detector" function. Such a non-gaussian optical device is commercially available from Lasiris, Inc. (St. Laurent, Quebec, Canada), Model No. SNF-501-H and SLH-501-H.

Figure 6:
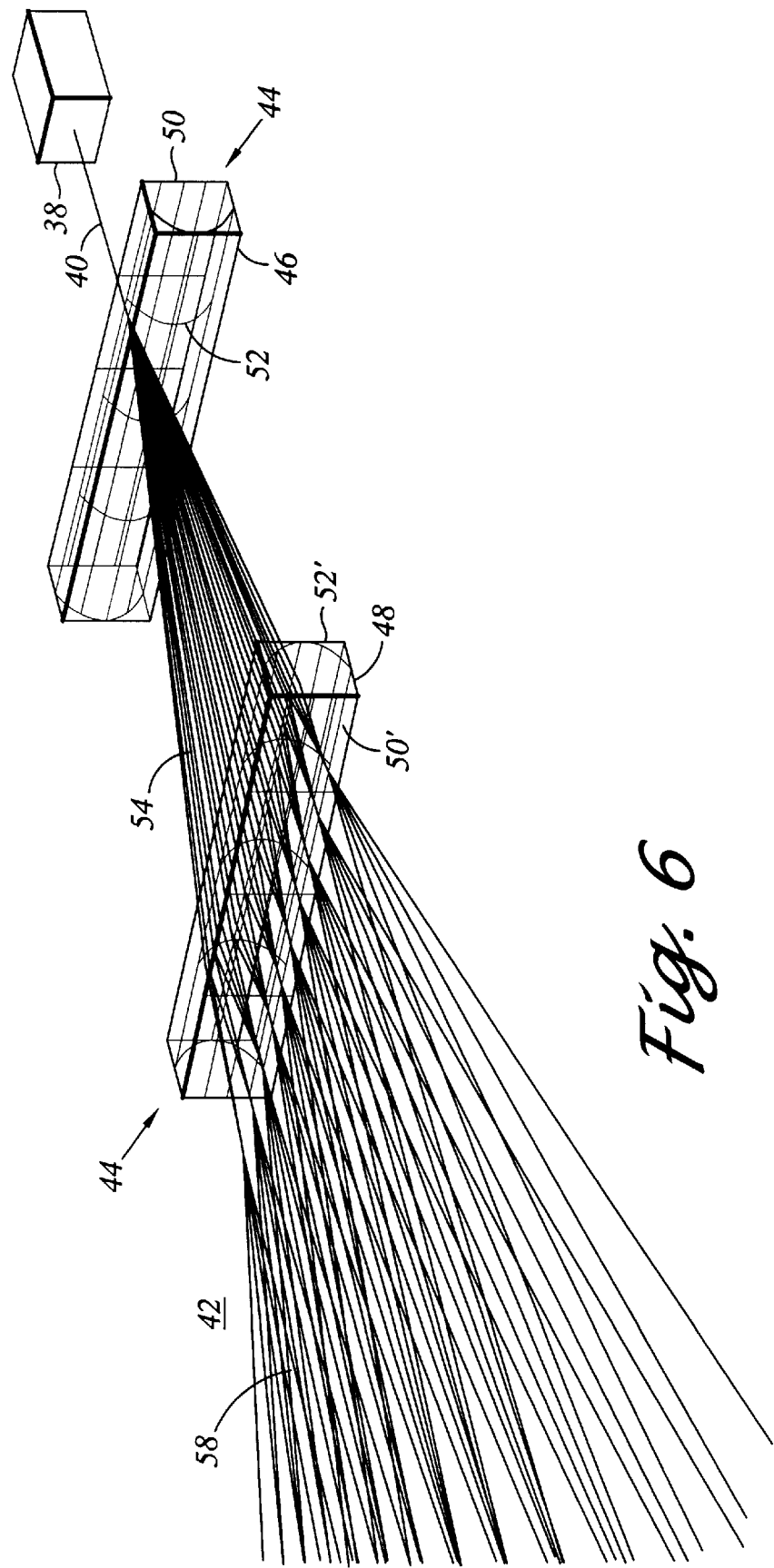
FIG. 6 is a perspective view showing the cylindrical optics of the apparatus of FIG. 5 and the light path through the cylindrical optics.

Reshaping can also be accomplished using optics 44 that are gaussian, in particular, cylindrical optics, edge detector optics or spherical optics. Cylindrical optics are preferred. A single planoconvex cylindrical lens is preferred. Alternatively, a system of two planoconvex cylindrical lenses is used. Referring to FIGS. 5 and 6, the cylindrical optics can comprise a first planoconvex cylindrical lens 46 and an optional second planoconvex cylindrical lens 48 which are substantially identical. Each planoconvex cylinder lens 46 and 48 has a planar face 50 and 50', respectively. Diametrically opposing each planar face 50 and 50' is a convex face 52 and 52', respectively. The lenses are made out of quartz or borosilicate glass. Dimensions of typical lens are between about to about 0.2" (l)×0.1" (w)×0.2" (d) to about 1" (l)×0.5" (w)×2" (d), with a preferred dimension of 0.5 inch (l)×0.1 inch (w)×0.2 inch (d). The focal length of the planoconvex cylinder lens is between about 3 mm to about 20 mm, with a preferred focal length between 5 mm and 6 mm. Satisfactory lenses are commercially available from Melles Griot Corp., Irvine, Calif., Part #01 LCP 000 or 01 LCP 124. The two planoconvex cylindrical lenses 46 and 48 are positioned in a front-to-front configuration. A filter 54 (not shown) can be placed between the lenses.

As shown in FIGS. 4A, 4B, and 5, light is introduced into the bottom surface 25 of the waveguide and not into an end. This permits use of non-optical quality waveguides, which reduces the cost of the system. Also, this allows use of larger waveguides because the dropoff problem associated with long waveguides can be overcome by causing relative movement between the waveguide and the laser light.

The intensity of the emission of light from a laser diode follows a gaussian distribution. Despite this gaussian distribution, there usually is substantially equal illumination over the entirety of the waveguide. When the analytical procedure is taken to the limits of its sensitivity for detection, it may be necessary to correct for uneven illuminations. One of ordinary skill in the art is familiar with mathematical formulas to compensate for the gaussian distribution of laser light intensity. In the alternative to mathematical correction, a light-emitting compound having an actual known emission is applied to the waveguide. This compound serves as an internal standard upon which to make corrections based upon the detected emission and actual known emission.

There can be a proximal prism 58 positioned at the end portion 56 of the waveguide 24 where light enters the waveguide. The purpose of this proximal prism 58 is to adjust the launch angle 26 of the slit beam into the waveguide so that it is less than the critical angle. Preferably, the prism adjusts the launch angle to provide the best signal-to-background ratio. The more desirable launch angles are from about 1 degree to about 39 degrees with 30 degrees being the most preferred.

Continuing to refer to FIG. 5, there optionally can be a coupling prism 60 at the distal portion 62 of the waveguide 24; i.e., the end of the substrate opposite the end where laser light exits the waveguide 24. The purpose of this coupling prism 60 is to bleed out the laser light 42 and evanescent waves 30 from the waveguide 24. In a configuration having coupling prisms 58 and 60 at both ends of the waveguide 24, the prisms serve the additional purpose of being a stage for holding the waveguide 24.

The coupling prisms are triangular blocks. Typically, the coupling prisms have dimensions from about 1 mm (l)×1 mm (w)×1 mm (d) to about 3 cm (l)×3 cm (w)×3 cm (d). The coupling prisms are made out of quartz or borosilicate glass. The index of refraction ranges from about 1.4 to about 1.6. A suitable prism known as a hemispherical prism is commercially available from Harrick Scientific, Ossining, N.Y.

Referring to FIG. 5, the interfaces between the prism 58 and 60 and the portions of the substrates 56 and 62 need to be substantially free from air bubbles. This is because air bubbles cause diffraction of the laser light resulting in background noise and a loss of laser intensity. One way to achieve a bubble free interface is to apply a coupling fluid to the interface. The coupling fluid has the same index of refraction as the prism. Coupling fluid can be commercially purchased from Cargille Laboratories under the name REFRACTIVE INDEX MATCHING FLUID. The use of coupling fluid has the additional benefit of enhancing the lateral field uniformity. Another way to achieve a bubble free interface is to apply pressure to the prism to urge it against the waveguide so as to force out any air bubbles. This can be achieved through a clamping mechanism.

In a preferred version of the invention, the coupling fluid is eliminated. This is accomplished by using a prism of high refractive index, such as one made of gadolinium, gallium, garnat, which has an index of refraction of 1.96. This is available from Optics for Research, of Coldwell, N.J., under Catalog No. ADG-6. In this version of the invention, a clamp system can be used to bring the high index of refraction prism into close proximity of the waveguide, wherein the light is launched into the waveguide through a small air gap.

Figure 8A:
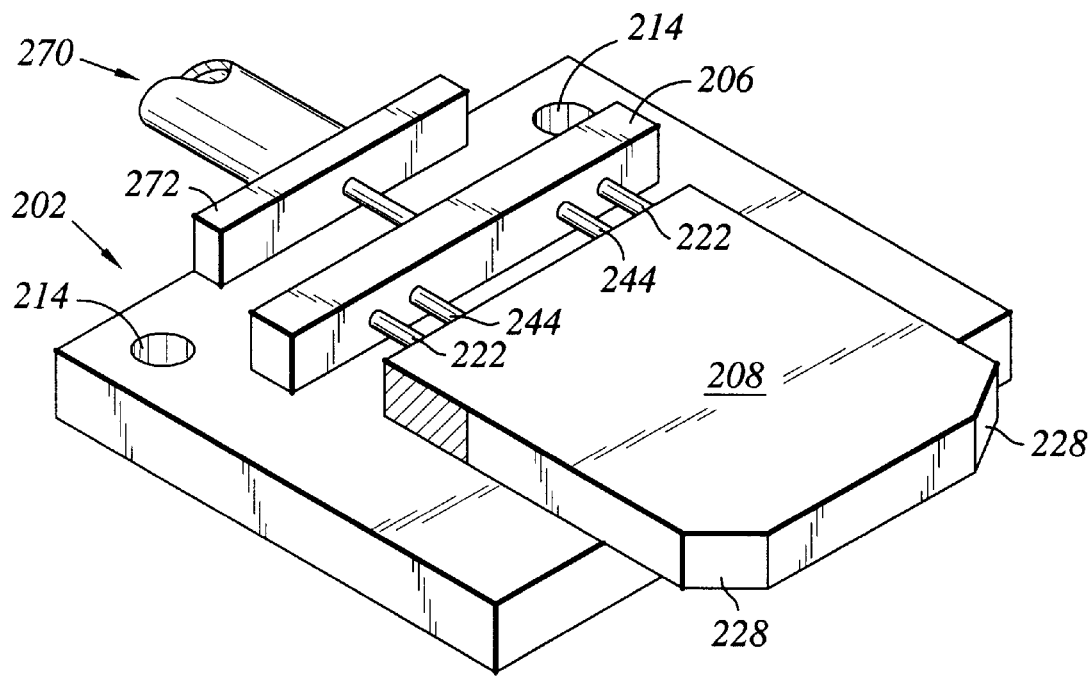
FIG. 8A is a perspective view of a mechanism for directly coupling a laser light source to a waveguide.
Figure 8B:
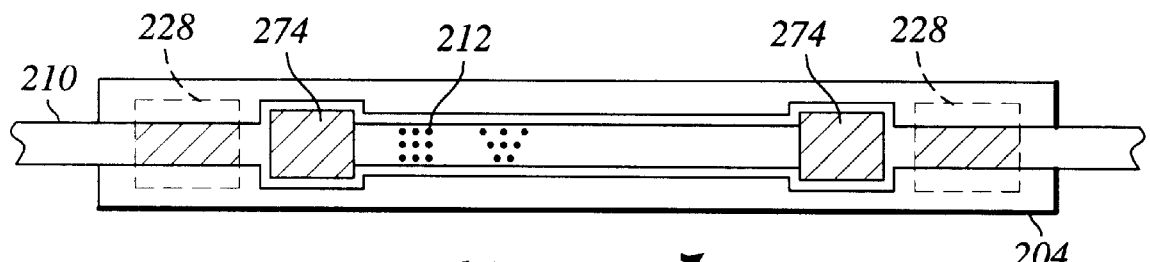
FIG. 8B is a side elevation view, partly cut away, of the mechanism of FIG. 8A.

A suitable clamping system 202 is shown in FIGS. 8A–8D. The clamping system 202 comprises a base 204 that supports an actuator bar 206 and a detector housing 208. As shown in FIG. 8B, a detector comprising an elongated film 210 with a plurality of probes 212 thereon is passed through the detector housing 208, in which it is clamped and laser light launched into it for detection purposes. The base plate 204 is mounted to a work bench (not shown) with fasteners (not shown) extending through mounting 214. The actuator bar 206 is held to the base plate by fasteners (not shown) that extend through oval holes 216 (shown in FIG. 8C only) in the actuator bar 206. The holes 216 being oval shaped allow relative movement between the actuator bar 206 and the base plate 204.

Figure 8C:
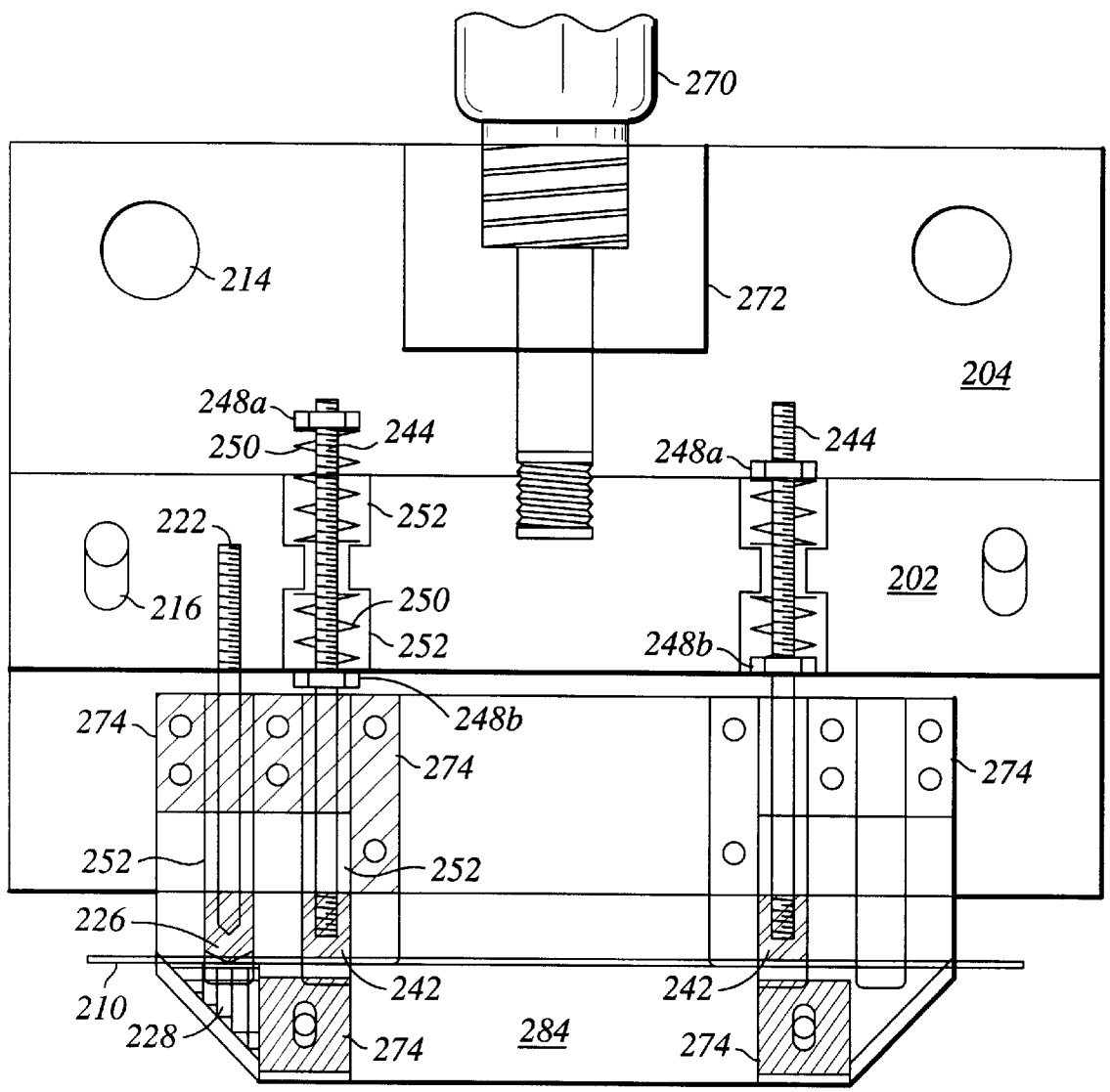
FIG. 8C is a top plan view, partly in section, of the mechanism of FIG. 8A.
Figure 8D:
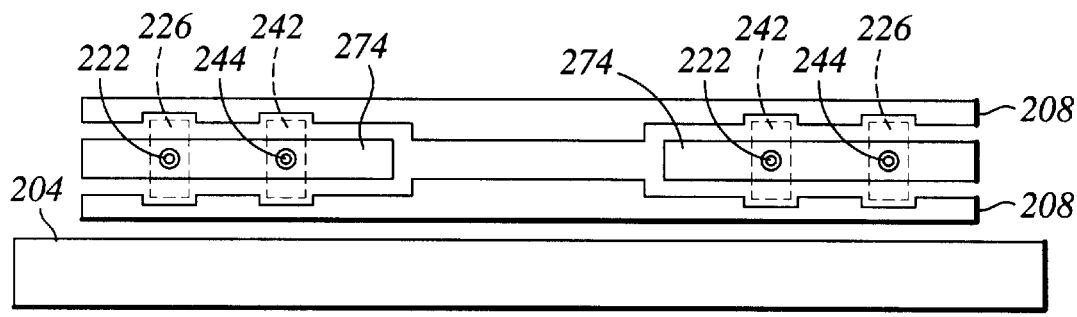
FIG. 8D is a side elevation view, similar to the view of FIG. 8B of the mechanism of FIG. 8A with a portion of the mechanism cut away for clarity.

Threaded into the actuator bar are two push rods 222 having at their distal end an RTV silicone pressure foot 226 that is used for pressing a waveguide detector against a prism 228 supported by the housing 208. FIG. 8C shows only one of the two identical push rods 222. There are provided two prisms 228, one associated with each of the push rods 222.

Each prism 228 has associated therewith a light trap bar 242 which is pushed in place by a light trap push rod 244 that "floats" in the actuator bar 206. The amount of float is set by upper 248a and lower 248b nuts threaded onto the light trap push rods 244. The amount of movement is controlled with upper and lower springs 250 which sit in recesses 252 in the actuator bar 206. The four rods 222 and 244 move relative to the housing 208 in grooves 252 formed in the housing.

The movement of the actuator bar is caused by a pneumatic linear actuator 270 that is supported on the base by a mounting block 272. The linear actuator 270 is threaded into the actuator bar 206. Rather than using a pneumatic linear actuator, as a less expensive alternative, there can be used a spring actuated cam.

The relative position of the components is controlled by use of spacer bars 274 mounted in the housing 208.

Light emitted from the probes on the waveguide is detected in a region 284 by a light detector.

Detection device, imaging optics and confocal lens— Referring to FIG. 5, a detector 64 used to detect emitted light can be a charge transfer device ("CTD"). A CTD has a two-dimensional multi-column layout, i.e., pixels. When struck by light, each column (pixel) builds up charge and products an output signal. The light emitted at a discrete area on the waveguide will be focused onto the active detecting surface of the CTD and will illuminate one or more pixels depending upon the area emitting and the magnification and focus of the collection optics. The charge accumulated on all illuminated pixels is added together into an output signal. This addition of cumulative charges is known as "binning." There are two principal types of CTDs; namely, a charge coupled device ("CCD") and a charge injector device ("CID"). CCDs are commercially available from Photometrics Ltd., Tucson, Ariz., and Princeton Instruments, Princeton, N.J.

The detector 64 can be equipped with imaging optics, including a confocal lens 66. The detector can be equipped with filters to block out light other than that at a selected wavelength. Such filters are used when the assay employs different light-responsive compounds that emit light at different wavelengths.

Target analytes—An exemplary list of target analytes which can be tested for are: (1) hormones, including, but not limited to, insulin, follicle stimulating hormone, progesterone, estrone, testosterone, adrenalin (epinephrine) and noradrelin (norepinephrine); (2) illegal drugs, including, but not limited to, amphetamines, methaphetamines, mescaline, lysergic acid diethylamide (LSD), morphine and N-ethyl-3-piperidylbenzilate; (3) immune factors, including, but not limited to, interferon, lucotrienes and macrophage coating stimulating factor; (4) cancer related molecules including, but not limited to, myelomas, neoembryonic antigens, epidermal like growth factor, insulin like growth factor and tumor narcosis factor; (5) antibodies to viruses and diseases, including, but not limited to, antibodies to hepatitis, AIDS (acquired immune deficiency disease), polio, measles, diphtheria and yellow fever; (6) toxins and poisons, including, but not limited to, arsenic, strychnine and bacterial endotoxins; and (7) miscellaneous blood components and proteins, including, but not limited to, immunoglobulins, complement proteins, low density lipoproteins, high density lip-proteins, cholesterol and serum albumin.

Methodology—To run an assay, the sample is optionally pre-reacted with one or more light-responsive compounds. The light-responsive compound can be either a light-emitting compound or a light-modulating compound. Where the sample is not pre-reacted with a light-emitting compound, the probes on the waveguide include a light-emitting compound or a developer is used. Where a light-emitting compound is bonded to sample, it can be desirable to include a light-modulating compound with the probes on the waveguide.

The next step is to apply sample to the waveguide. This can be done by dipping, pouring, brushing or spraying. The waveguide is subjected to appropriate conditions to facilitate the formation of a complex between probe and any target analyte in the sample. This can require incubation at an elevated temperature, increasing or decreasing pH or salt concentration. For example, if the probe is an antibody, it can be necessary to incubate at an elevated temperature. If the probe is an oligonucleotide, it can be necessary to apply a wash solution to reduce salt concentration. The necessary reaction conditions and times are apparent to those of ordinary skill in the art based upon the particular target analyte and specific binding partner.

If a developer (e.g., a monoclonal antibody or target analyte analog with a light-responsive compound attached to it) is used, it is applied to the waveguide in the same manner as sample, simultaneously or sequentially, depending on the assay type. The waveguide is then subjected to appropriate conditions to facilitate the formation of complex between the developer and target analyte-probe as described above with respect to sample-probe complex formation.

A laser light can be launched into the waveguide with the sample remaining on the waveguide. However, preferably the bulk of the sample is removed from the waveguide before detection, such as by holding the waveguide vertically and allowing residual sample to drain or drip off the waveguide. If desired, all of the liquid portion of the sample can be removed from the waveguide by active drying step, such as by application of heat. Advantages of removing the bulk of the sample, and preferably substantially all of the sample, from the waveguide relate to improved accuracy of results from the invention. By removing the sample, adverse microenvironmental effects of any solvents in the sample are minimized. Moreover increased photostability of detection dyes results. Constituents of the sample can adversely affect the detection dye, and can affect the chemistry of the photo detection system. Also, removal of the sample before detection increases light containment within the waveguide.

Although the bulk of the sample is removed from the waveguide, it is possible to leave a small portion of the sample on the waveguide without greatly adversely effecting the accuracy of the results. Thus, the analysis can be conducted "wet."

Being able to conduct the analysis wet is one of the advantages of this version of the invention in that it saves the time and money of a drying step. Further, not having a drying step simplifies automated processing equipment. When running the analysis wet, the laser light source emits light between about 600 nanometers to about 960 nanometers. Light of a wavelength greater than 960 nanometers interacts with water in the wet sample to possibly lead to spurious results.

Optionally, the waveguide can be substantially completely dried before passing a laser beam into it. It is desirable to dry the waveguide when the chosen light-responsive compound requires light of a wavelength greater than 960 nanometers or to improve sensitivity of the analysis. Optionally, a sol gel overcoat onto the waveguide, if one was not put on prior to applying sample. This is desirable where high sensitivity is required in that sol gel will reduce any diffuse reflectance.

A laser beam is passed into the waveguide and the emission of any light from each discrete area is detected.

A significant advantage of the present invention is it can be used with elongated waveguides. To do this, it is necessary to overcome the dropoff problem associated with long waveguides. This dropoff problem results from loss of light intensity as the laser light is propagated along the length of the waveguide. This can be overcome by causing relative movement between the waveguide and the laser light, either by moving the waveguide relative to the fixed laser light beam, moving the laser light beam along a fixed waveguide or a combination of the techniques. For example, the waveguide can be in the form of a tape which is spooled across a detecting laser light beam. This feature of the present invention requires that the laser light be introduced into one of the planar surfaces of the waveguide, rather than an end edge.

Figure 9:
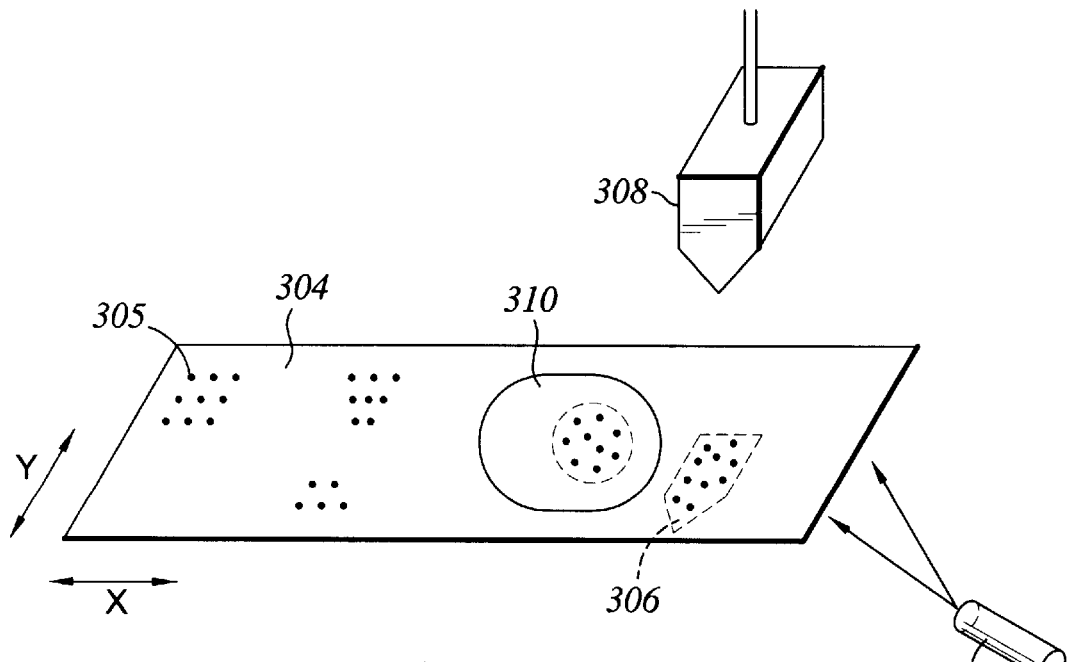
FIG. 9 is a schematic view of a system according to the present invention.

With reference to FIG. 9, a fixed laser light source 302 can be used for a large film waveguide 304 having a plurality of probes 305 thereon. A prism 306 of the detection system is beneath the waveguide 304 and the waveguide is held against the prism by a knife-edged pressure foot 308. The region of the waveguide being illuminated by the laser light, and from which emissions are detected, is region 310. The waveguide can be moved in directions represented by double-headed arrows X and Y in FIG. 9, relative to the fixed laser light source 302, so that the entire array of probes on the waveguide can be illuminated and detected.

Modified method of use for epi-illumination—A version of this invention uses epi-illumination instead of passing a laser light into the substrate. This version of the invention follows the procedure previously discussed with the following modifications. Light-responsive compounds are selected which emit light at a wavelength different from that of the incident light. The waveguide is coated with a sol gel having an index of refraction substantially equal to that of the waveguide. A light is passed into the waveguide at an angle about perpendicular to the plane of the waveguide. The detector is equipped with a filter to block out light at a wavelength equal to the wavelength of the incident light. The detection of light at a discrete area indicates the presence of the particular target analyte in the sample.

EXAMPLE 1

This example demonstrates an attempt to do quantitative analysis for Digoxin according to the present invention.

A waveguide was formed from polystyrene film, 4 mil thick. Printed onto it in spots was avidin. Multiple samples containing a predetermined concentration of free Digoxin were prepared, using Digoxin as a target analyte. The samples were spiked with a $10^{-9}$ molar concentration of biotinylated Digoxin, which functioned as an analog to compete with the free Digoxin for binding to a fluorescently labelled monoclonal antibody, which was also spiked into the sample. The spiked samples were applied to the waveguide, and allowed to react with the avidin spots. The fluorescent dye used was DBCY5 synthesized with an NHS ester group for reaction with the amine group on the antibody. The dye labelled antibody bonded to the target analyte was then washed away leaving the fluorescently labelled antibody which had bound to the biotinylated Digoxin. The assay was conducted with a phosphate buffer to maintain a pH at about 7.6. After each sample was applied to the waveguide, the sample was provided with a 30-minute incubation period, and then blown dried.

Laser light from a gallium aluminum arsenide laser at about 670 nanometers was applied to the waveguide, and used for activating the dye.

Figure 7:
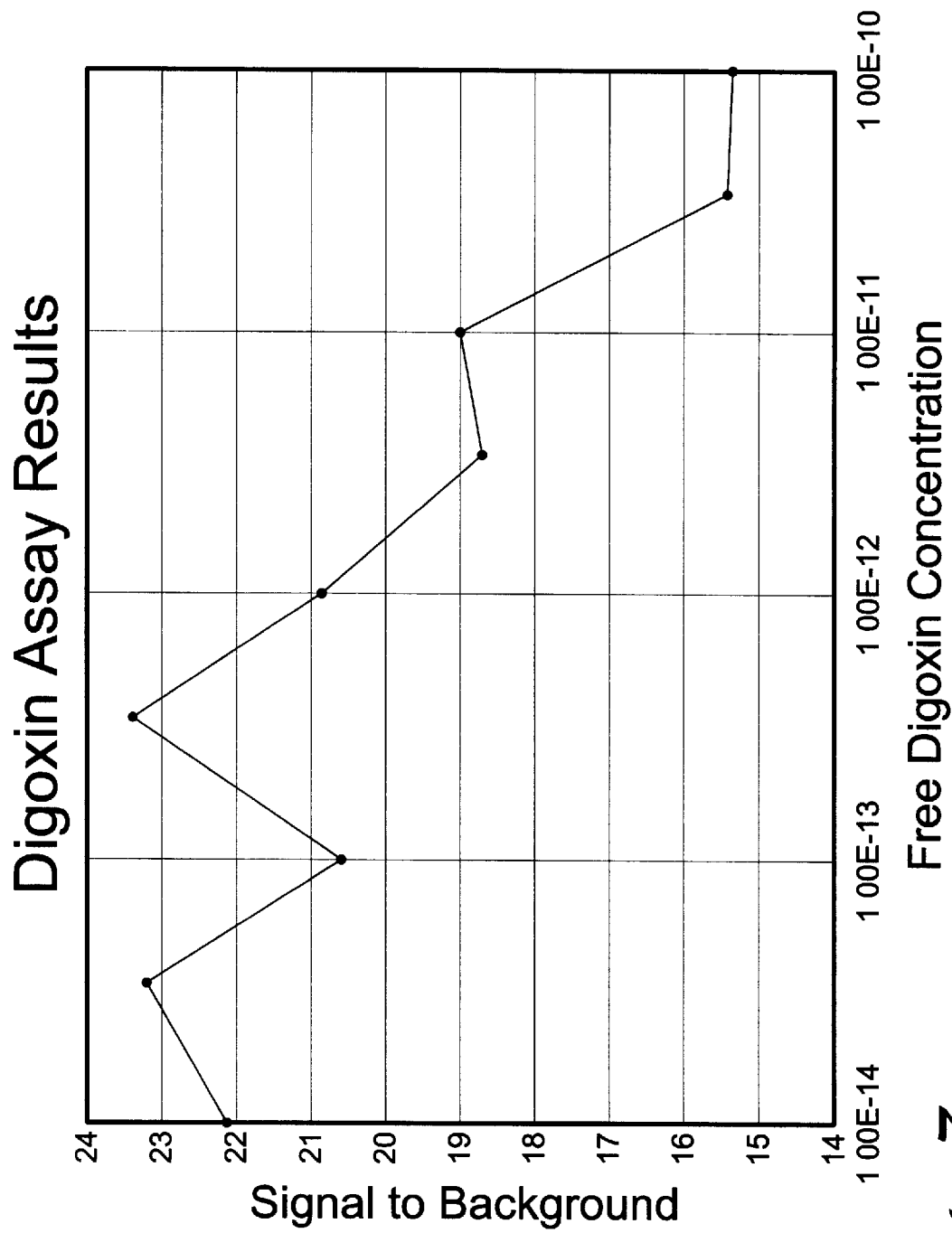
FIG. 7 is calibration curve for a competitive immunoassay to quantitatively analyze Digoxin in a sample analyzed according to the present invention.

FIG. 7 presents the response curve from the test. The curve shows this technique was good at qualitative analysis, but of limited success at quantitative analysis. Later experiments revealed that for accurate quantitative analysis, it is preferred that the specific binding partner be covalently bonded to the waveguide.

EXAMPLE 2

This example demonstrates qualitative detection of a DNA oligonucleotide target analyte.

The waveguide used was made of polypropylene film, about 3 ml thick. A short sequence oligonucleotide complementary to the target analyte was covalently coupled to the waveguide using acyl fluoride coupling, and served as the probe. Both the target and the probe were about 10 to 15 nucleotides long. The target analyte was pretreated with CY5 dye, and also provided with an avidin linkage. The CY5 dye is the same as the DBCY5 dye shown above, without the two outermost benzene rings. The probe was provided with a biotin linkage. The waveguide had on one of its surfaces a layer of rows and columns of spots of the probe. The sample was applied to the waveguide, incubated, and dried. A laser provided light at 670 nanometers.

The waveguide successfully differentiated between samples containing the target nucleotide and samples not containing the target nucleotide. When the results detected were displayed on a computer monitor, a lighted spot indicated attachment of the target oligonucleotide to the probe, while a dark spot meant that no target oligonucleotide was in a sample.

The system of the present invention has significant advantages. It allows for the inexpensive and fast analysis of samples for multiple analytes using a straightforward and simple process. It can accurately detect target analytes. Moreover, the detector used in the system can be manufactured by conventional printing equipment. The method can be automated with non-complex equipment, it can be used for both qualitative and quantitative detection.

As a most preferred version of the present invention, as presently envisioned, the waveguide is made of polystyrene, where the specific binding partner is avidin attached to the polystyrene with a photocoupling technique such as that available from Surmodics, Inc., formerly BSI Surface Modification Sciences, of Eden Prairie, Minn., and sold under the trademark "PHOTOLINK". A sample is treated with an antibody to the target analyte, the antibody having attached to it DBCY5 fluorophore. An analog to the target analyte is used, the analog comprising the target analyte bound to biotin. The laser is a gallium aluminum arsenide laser emitting light at about 670 nanometers. In this preferred method, the target analog bound to the biotin attaches to the avidin on the waveguide through an avidin-biotin linkage. The analog carries with it an amount of DBCY5 labelled antibody which is indicative of the competition between analyte and analog for antibody binding sites. The more target analyte present in the sample, the less analog binds, and the weaker the emitted signal.

Although the present invention has been described in considerable detail with reference to certain preferred versions thereof, other versions are possible. For example, a band pass filter can be used on the light from the laser to be certain that only light of a desired wavelength passes into the waveguide, i.e., only light of a wavelength to which the dye is responsive. Similarly, an emission band filter can be provided between the waveguide and the detection apparatus, for filtering out the light of all wavelengths other than those expected to be emitted by the chosen fluorophore. Therefore, the spirit and scope of the appended claims should not be limited to the description of preferred versions contained herein.

What is claimed is:

1. A method for detecting a target analyte in a sample, the method comprising the steps of:
    a) providing a detector comprising a waveguide having opposed planar surfaces with a plurality of discrete probes on at least one of the planar surfaces, each probe including a specific binding partner for a selected analyte, at least one of the probes being a responsive probe that includes a specific binding partner for the target analyte;
    b) applying the sample to the detector such that the target analyte binds to its specific binding partner;
    c) passing laser light into a first selected location of one of the planar surfaces of the detector so that evanescent light radiates from the waveguide and impinges on at least some of the probes, wherein light, if any, emitted from a probe with target analyte bound thereto is different from the light, if any, emitted by the same probe without target analyte bound thereto;
    d) detecting emission of light from at least one first selected probe;
    e) causing relative movement between the laser light and the detector;
    f) passing laser light into a second selected location of one of the planar surfaces of the detector, so that evanescent light radiates from the waveguide and impinges on at least some of the probes, wherein the second selected location is different from the first selected location, wherein light, if any, emitted from a probe with a target analyte bound thereto is different from the light, if any, emitted by the same probe without target analyte bound thereto; and
    g) detecting emission of light from at least one second selected probe which is different from the first selected probe.

2. A method for detecting a target analyte in a sample, the method comprising the steps of:
    a) providing a detector comprising a waveguide having a planar surface with a plurality of discrete probes on the planar surface, each probe including a specific binding partner for a selected analyte, at least one of the probes being a responsive probe that includes a specific binding partner for the target analyte;
    b) applying the sample to the detector such that the target analyte binds to a specific binding partner;
    c) passing laser light into the detector at a plurality of selected locations on the planar surface by causing relative movement between the waveguide and the laser light so that evanescent light radiates from the waveguide and impinges on at least some of the probes, wherein light, if any, emitted from a probe with target analyte bound thereto is different from the light, if any, emitted by the same probe without target analyte bound thereto; and
    d) detecting emission of light from the probes.

3. The method of claim 2 wherein a probe without target analyte bound thereto emits substantially no light and a probe with target analyte bound thereto emits sufficient light to be detected during the step of detecting.

4. The method of claim 3 comprising the step of attaching to the target analyte, before or after the target analyte binds to its specific binding partner, a light-emitting compound, wherein the light-emitting compound emits light when the laser light is passed into the detector.

5. The method of claim 4 wherein the light-emitting compound is attached to the target analyte before the sample is applied to the detector.

6. The method of claim 2 wherein each probe includes a light-emitting compound.

7. The method of claim 2 wherein the probes include a light-emitting compound, and the method comprises the step of attaching to the target analyte, before or after the target analyte binds to its specific binding partner, a light-modulating compound, wherein the light-modulating compound affects the light emitted by the light-emitting compound when the laser light is passed into the detector.

8. The method of claim 7 wherein the light-modulating compound is a quencher that prevents the light-emitting compound from emitting light.

9. The method of claim 7 wherein the light-modulating compound is attached to the target analyte before the sample is applied to the detector.

10. The method of claim 2 including the additional step of removing a substantial portion of the sample from the detector before passing laser light into the detector.

11. The method of claim 1 wherein the step of causing relative movement comprises moving the waveguide relative to the laser light while the laser light is maintained in fixed position.

12. A method for detecting a target analyte in a sample, the method comprising the steps of:
   a) providing a detector comprising a waveguide having a planar surface thereon and having a plurality of discrete probes, each probe including a specific binding partner for a selected analyte, a plurality of the probes being a responsive probe that includes a specific binding partner for the target analyte;
   b) exposing the probes to (i) the sample and (ii) an analog of the target analyte, the analog being capable of binding to the same specific binding partner to which the target analyte can bind, so that the analog and the target analyte competitively bind to the responsive probes;
   c) passing laser light into the detector at a plurality of selected locations on the planar surface by causing relative movement between the waveguide and the laser light so that evanescent light radiates from the waveguide and impinges on the probes, wherein light, if any, emitted from a probe with target analyte bound thereto is different from the light, if any, emitted by the same probe with the analog bound thereto; and
   d) detecting emission of light from the probes.

13. The method of claim 12 wherein the analogs include a light-emitting compound so that only responsive probes with analog bound thereto emit light.

14. The method of claim 12 including the additional step of removing a substantial portion of the sample from the detector before passing laser light into the detector.

15. A method for analyzing multiple samples for the same target analyte, the method comprising the steps of:
   a) providing a detector comprising a waveguide having a planar surface with a plurality of discrete probes thereon, at least some of the probes being a responsive probe that includes a specific binding partner for the target analyte;
   b) treating each sample with a different light-emitting compound so that the light-emitting compounds attach to the target analyte in the samples to form conjugates;
   c) applying the samples to the detector such that the conjugates bind to the responsive probes;
   d) passing laser light into the detector at a plurality of selected locations on the planar surface by causing relative movement between the waveguide and the laser light so that evanescent light radiates from the waveguide and impinges on the responsive probes resulting in light being emitted by the light-emitting compounds, wherein the different light-emitting compounds emit different light; and
   e) detecting emission of light from the probes.

16. The method of claim 15 wherein the different light-emitting compounds emit light that differs in the wavelength, intensity or color.

17. A method for detecting multiple target analytes in a sample, the method comprising the steps of:
   a) providing a detector comprising a waveguide having a planar surface with a plurality of different discrete probes thereon, each probe including a specific binding partner for a selected analyte, at least some of the probes being capable of binding to a corresponding target analyte;
   b) applying the sample to the detector such that the target analytes bind to their corresponding specific binding partner;
   c) passing laser light into the detector at a plurality of selected locations on the planar surface by causing relative movement between the waveguide and the laser light so that evanescent light radiates from the waveguide and impinges on the probes, wherein light, if any, emitted from a probe with target analyte bound thereto is different from the light, if any, emitted by the same probe without target analyte bound thereto; and
   d) detecting emission of light from the probes.

18. The method of claim 17 wherein a probe without target analyte bound thereto emits substantially no light and a probe with target analyte bound thereto emits sufficient light to be detected during the step of detecting.

19. The method of claim 17 comprising the step of treating the target analytes with a plurality of different light-emitting compounds, each light emitting compound attaching to a corresponding target analyte, wherein the light-emitting compounds emit light when the laser light is passed into the detector, the different light-emitting compounds emitting different light.

20. The method of claim 17 wherein the light-emitting compounds are attached to the target analyte before the sample is applied to the detector.

21. The method of claim 4 wherein the light-emitting compound is a fluorophore.

22. The method of claim 2 wherein the laser light has a wavelength of from about 600 to about 960 nanometers.

23. The method of claim 2 wherein the specific binding partners are covalently bonded to the waveguide.

* * * * *